(12) United States Patent
Wu

(10) Patent No.: US 12,257,171 B1
(45) Date of Patent: Mar. 25, 2025

(54) COCK RING

(71) Applicant: Xiaoxuan Wu, Guangdong (CN)

(72) Inventor: Xiaoxuan Wu, Guangdong (CN)

( * ) Notice: Subject to any disclaimer, the term of this patent is extended or adjusted under 35 U.S.C. 154(b) by 0 days.

(21) Appl. No.: 18/782,067

(22) Filed: Jul. 24, 2024

(51) Int. Cl.
*A61F 5/41* (2006.01)
*A61H 19/00* (2006.01)
*A61H 21/00* (2006.01)

(52) U.S. Cl.
CPC .............. *A61F 5/41* (2013.01); *A61H 19/30* (2013.01); *A61H 21/00* (2013.01); *A61F 2005/414* (2013.01)

(58) Field of Classification Search
CPC ........ A61H 19/00; A61H 19/30; A61H 19/32; A61H 19/40; A61H 19/44; A61H 19/50; A61H 21/00; A61F 2005/411; A61F 2005/414; A61F 2005/417; A61F 2005/418; A61F 5/41
USPC ......................................... 600/38, 39, 41, 40
See application file for complete search history.

(56) References Cited

U.S. PATENT DOCUMENTS

| | | | | |
|---|---|---|---|---|
| 5,370,131 A | * | 12/1994 | Hess | A61F 6/04 128/842 |
| 5,387,179 A | * | 2/1995 | Crivellaro | A61F 5/41 600/38 |
| 6,039,750 A | * | 3/2000 | Kubalak | A61F 2/0054 128/DIG. 25 |
| 6,102,043 A | * | 8/2000 | Johnson | A61F 6/04 128/918 |
| 2017/0360653 A1 | * | 12/2017 | Marshall | A61H 21/00 |

\* cited by examiner

*Primary Examiner* — Samuel G Gilbert
(74) *Attorney, Agent, or Firm* — Justin Lampel

(57) ABSTRACT

A cock ring is provided in the disclosure, which includes a penis sleeve part, a first stimulating part and a second stimulating part which are flexibly provided in sequence. According to the cock ring according to the disclosure, the penis sleeve part is sleeved on the penis, so that the testicles or perineum contacts and abuts against the first stimulating part, and the second stimulating part is inserted into the anus, and thus when the first stimulating part and the second stimulating part function in stimulating at the same time, the testicles and the anus can be stimulated at the same time, and use comfort of users is improved.

6 Claims, 6 Drawing Sheets

COCK RING

FIELD OF THE INVENTION

The disclosure relates to the field of sex toys, in particular to a cock ring.

BACKGROUND OF THE INVENTION

A cock ring (also known as penis ring and persistent ring) is a type of sex aid for male sexual health, which usually serve to encircle a root of penis or testis. Its main function is to limit blood backflow from penis with a physical pressure, thus thereby helping the male maintain an erect state, delay ejaculation and enhance sexual experience. The cock rings are generally made of flexible materials such as silicone, rubber or plastic and some of them can be made of metal materials, so as to provide different degrees of pressure and stimulation.

An existing cock ring provides effects of prolonging erection duration, increasing sexual pleasure and enhancing erection hardness through various materials, designs and functions, which is suitable for users with different needs. However, the existing cock ring is only designed with a ring part that acts on the penis, which indicates that it mainly focuses on pressure application and stimulation on the root of the penis, and does not involve use of anus, thus affecting stimulation effect of the cock ring.

DESCRIPTION OF THE INVENTION

In view of the above, it is necessary to provide a cock ring that can stimulate both penis and anus at the same time to solve the problem above.

A cock ring is provided in an embodiment of the disclosure, which includes a penis sleeve part, a first stimulating part and a second stimulating part which are flexibly provided in sequence.

The penis sleeve part is configured to be sleeved on penis, the first stimulating part is configured to contact and abut against testis or perineum for stimulating the testis or perineum, and the second stimulating part is configured to be inserted into the anus for stimulating the anus.

In at least one embodiment of the disclosure, the penis sleeve part includes a first ring and a second ring.

The first ring is arranged at an end of the first stimulating part, the second ring is arranged on the first ring, and the first ring and the second ring are configured to be sleeved on the penis.

In at least one embodiment of the disclosure, the penis sleeve part further includes a first connecting part.

Two ends of the first connecting part are respectively arranged on the first ring and the second ring for flexibly connecting the first ring and the second ring.

In at least one embodiment of the disclosure, the penis sleeve part includes a first ring, a second ring and a third ring.

Two ends of the first ring are respectively arranged on the first stimulating part to enclose to form a first opening, two ends of the second ring are respectively arranged on the first ring, and two ends of the third ring are respectively arranged on the first ring, and the second ring and the third ring enclose to form a second opening, and the third ring and the first ring enclose to form a third opening.

The penis is inserted through the first opening and the second opening, and the testis or perineum is carried between the first opening and the third opening and abuts against the first stimulating part.

In at least one embodiment of the disclosure, the first ring, the second ring and the third ring are annularly arranged at equal intervals.

In at least one embodiment of the disclosure, the first stimulating part includes an accommodating part and an abutting part.

The accommodating part is provided with a first accommodating cavity for accommodating a stimulation component, and the abutting part is attached to the accommodating part for contacting and abutting against the testis or perineum.

In at least one embodiment of the disclosure, the abutting part includes a plurality of protrusions, and the plurality of protrusions are arranged in parallel for contacting and abutting against the testis or perineum.

In at least one embodiment of the disclosure, the second stimulation part includes an insertion end and a stimulation end.

The insertion end is configured to be inserted into anus of a human body, and the stimulation end is provided with a second accommodating cavity for accommodating a stimulation component.

A cross-sectional area of the insertion end gradually increases in a direction from the insertion end to the stimulation end.

In at least one embodiment of the disclosure, the cock ring further includes a second connecting part, and both ends of the second connecting part are respectively arranged on the first stimulating part and the second stimulating part.

In at least one embodiment of the disclosure, the second connecting part is a flexible strip structure for the second stimulating part to be bent relative to the first stimulating part.

According to the cock ring according to the disclosure, the penis sleeve part is sleeved on the penis, so that the testicles or perineum contacts and abuts against the first stimulating part, and the second stimulating part is inserted into the anus, and thus when the first stimulating part and the second stimulating part function in stimulating at the same time, the testicles or perineum and the anus can be stimulated at the same time, and use comfort of users is improved.

BRIEF INTRODUCTION OF THE DRAWINGS

Figure 1:
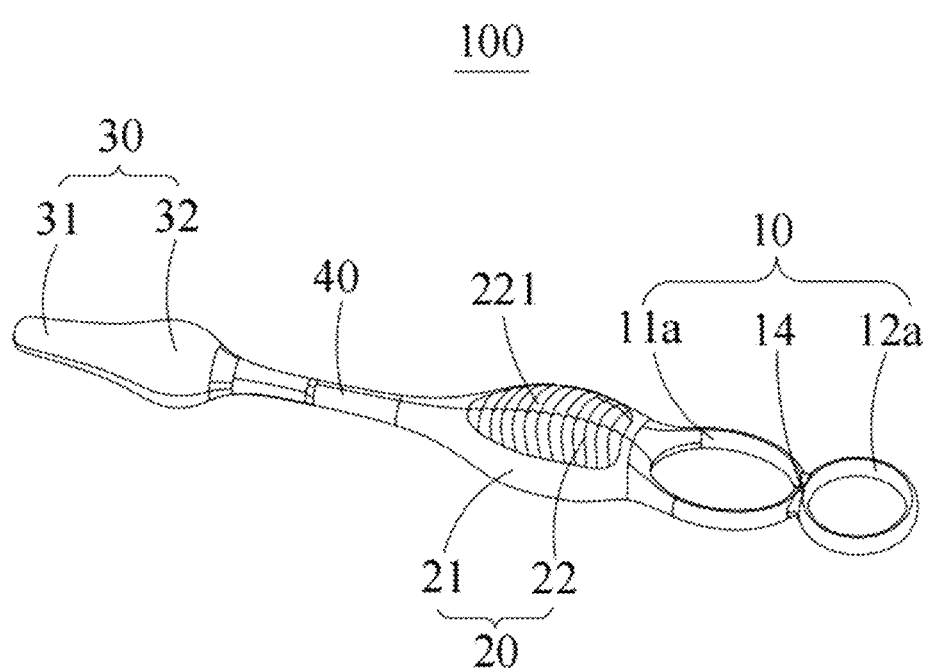
FIG. 1 is a schematic perspective structural view of a cock ring in a first perspective according to an embodiment of the disclosure.

Reference numbers of main components are as follows:
100. Cock Ring; 10. Penis Sleeve Part; 11a, 11b. First Ring; 12a, 12b. Second Ring; 13b. Third Ring; 14. First Connecting Part; 10a. First Opening; 10b. Second Opening;

10c. Third Opening; 20. First Stimulating Part; 21. Accommodation Part; 22. Abutting Part; 221. Protrusion; 30. Second Stimulating Part; 31. Insertion End; 32. Stimulating End; 40. Second Connecting Part; 50. Control Switch.

DETAILED DESCRIPTION OF THE PREFERRED EMBODIMENTS

In the following, embodiments of the disclosure will be described in detail in connection with the drawings; obviously, the described embodiments are intended to be only a part of the embodiments of the disclosure, but not all of them.

It should be noted that when a component is referred to be "connected" to another component, it may be directly connected to another element or an intervening component may exist at the same time. When a component is referred to be "provided" on another component, it may be directly provided on another component or an intervening component may exist at the same time. Terms "top", "bottom", "upper", "lower", "left", "right", "front" and "back" and similar expressions used herein are for illustration purposes only.

Some embodiments of this disclosure will be described in detail with reference to the drawings. The embodiments in the present disclosure and the characteristics in the embodiments described below can be combined mutually in the case of no conflict.

Referring to FIGS. 1 to 6, a cock ring 100 is provided in the disclosure, which includes a penis sleeve part 10, a first stimulating part 20 and a second stimulating part 30 which are flexibly provided in sequence. The penis sleeve part 10 is configured to be sleeved on penis, the first stimulating part 20 is configured to contact and abut against testis or perineum for stimulating the testis or perineum, and the second stimulating part 30 is configured to be inserted into the anus for stimulating the anus.

It should be noted that the cock ring 100 is generally made of silica gel, rubber, metal or other elastic materials, and it tightly encircles the root of the penis to reduce blood backflow from the penis during use, thus maintaining an erection state. However, the existing cock ring 100 can only be arranged around the penis, and cannot achieve higher stimulation effect.

In this disclosure, the penis sleeve part 10 is sleeved on the penis, so that the testicles or perineum contacts and abuts against the first stimulating part 20, and the second stimulating part 30 is inserted into the anus, so that when the first stimulating part 20 and the second stimulating part 30 start at the same time, the testicles or perineum and the anus can be stimulated at the same time, and use comfort of users is improved.

It should be noted that in the scheme above, the penis sleeve part 10, the first stimulating part 20 and the second stimulating part 30 are flexibly arranged in sequence, so that when the penis sleeve part 10 is sleeved on the penis, the second stimulating part 30 can be bent and conveniently inserted into the anus, so as to achieve effect of simultaneous stimulation. Preferably, the penis sleeve part 10, the first stimulating part 20 and the second stimulating part 30 are integrally formed of rubber or silica gel.

It can be understood that a stimulating position of the first stimulating part 20 mainly depends on a distance between the first stimulating part 20 and the second stimulating part 30. When the first stimulating part 20 is relatively far away from the second stimulating part 30 or when the user needs to stimulate the testicles, the testicles can be abutted against the first stimulating part 20 by extending the distance from the first stimulating part 20 to the second stimulating part 30. When the first stimulating part 20 is relatively close to the second stimulating part 30 or when the user needs to stimulate the perineum, the perineum can be abutted against the first stimulating part 20 by shortening the distance from the first stimulating part 20 to the second stimulating part 30.

Figure 2:
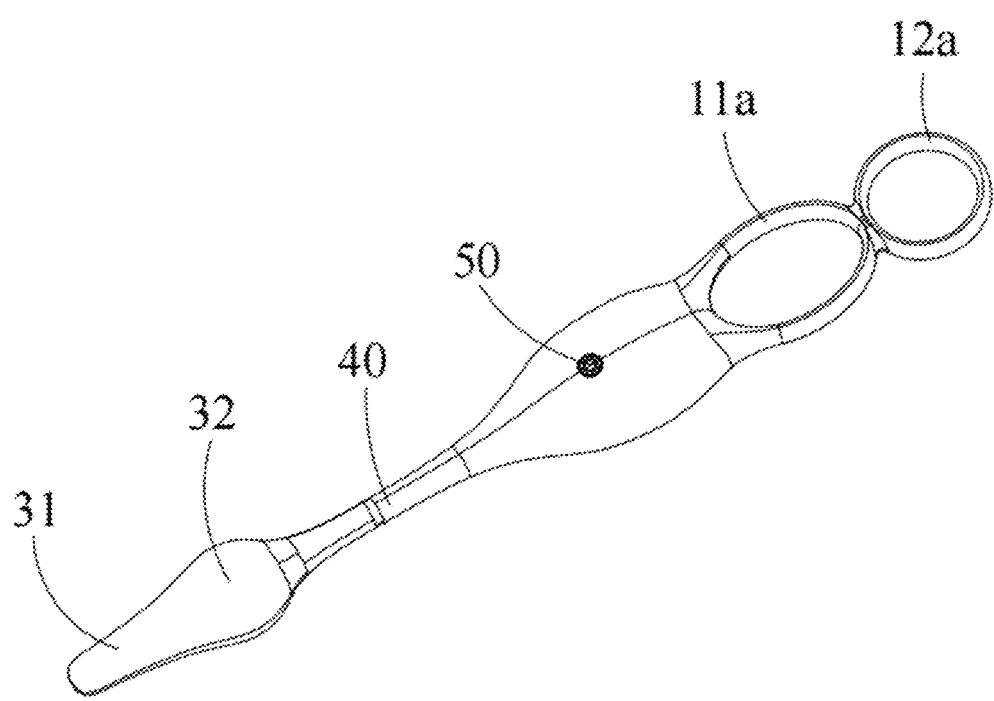
FIG. 2 is a schematic perspective structural view of a cock ring in a second perspective according to an embodiment of the disclosure.
Figure 3:
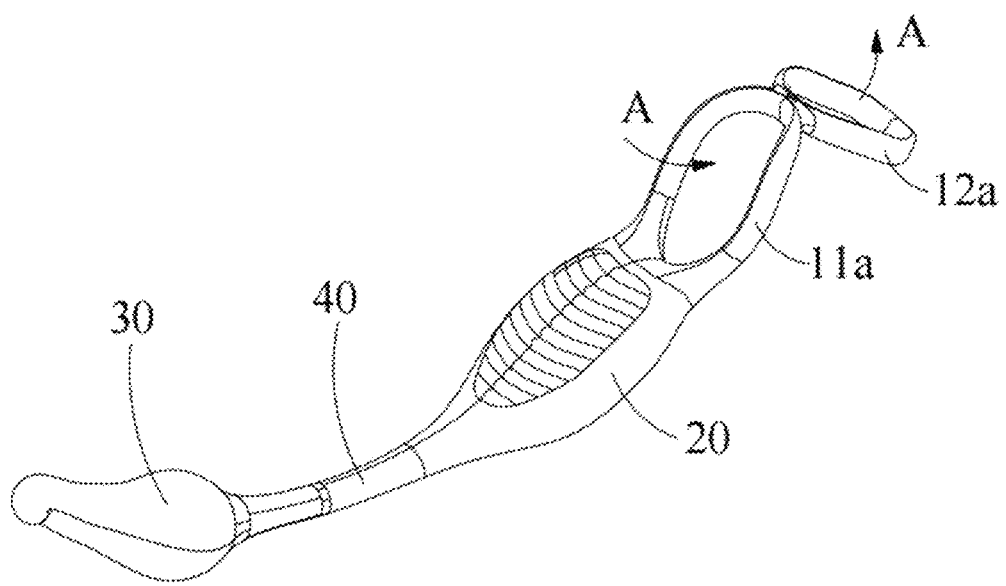
FIG. 3 is a schematic perspective structural view of a cock ring shown in FIG. 1 in use.

In an embodiment, referring to FIGS. 1 to 3, the penis sleeve part 10 includes a first ring 11a and a second ring 12a. The first ring 11a is arranged at an end of the first stimulating part 20, and the second ring 12a is arranged on the first ring 11a, and the first ring 11a and the second ring 12a are configured to be sleeved on the penis.

It should be noted that as shown in FIGS. 1 and 2, FIGS. 1 and 2 are state views of the cock ring 100 before use in an embodiment of the disclosure. In a specific embodiment, the penis sleeve part 10, the first stimulating part 20 and the second stimulating part 30 are arranged in a straight line, so that a problem of difficult production caused by a strange shape of the cock ring 100 can be avoided during manufacturing.

In a specific embodiment, stimulations of the first stimulating part 20 and the second stimulating part 30 include, but are not limited to, vibration, and can be in other stimulating manners such as heating.

Further, referring to FIG. 3, FIG. 3 is a state view of the cock ring 100 in a use state in an embodiment of the disclosure. At this time, human issue is located above the cock ring, the first ring 11a is folded upward at an external force from the user, the second ring 12a is folded downward at an external force from the user, and the second stimulating part 30 is folded upward. At this time, the penis is inserted into the first ring 11a and the second ring 12a in a direction A-A as shown in FIG. 3, and the penis is locked by the first ring 11a and the second ring 12a under a deformation force on the first ring 11a and the second ring 12a, so as to encircle and lock the penis and achieve effect of preventing the blood backflow. At this time, the testicles or perineum contacts and abuts against the first stimulating part 20, and the user bends the second stimulating part 30 downward along legs of the human body, so that the second stimulating part 30 bypasses crotch of the human body and extends and is inserted into the anus. At this time, first stimulating part 20 and the second stimulating part 30 are controlled to start, so as to achieve effects of limiting the blood backflow at the penis, stimulating the testis or perineum by the first stimulating part 20, and stimulating the anus by the second stimulating part 30 at the same time, with better stimulating effect compared with effect of limiting the blood backflow at the penis in related art.

In a specific embodiment, the cock ring 100 further includes a control switch 50 and a series of electronic elements, and the control switch 50 and electronic elements are electrically connected with stimulation components in the first stimulation part 20 and the second stimulation part 30, so as to achieve effect of controlling stimulation of the first stimulation part 20 and the second stimulation part 30. It should be noted that a scheme in which the switch 50 and electronic elements control starting of the first stimulating part 20 and the second stimulating part 30 is a scheme in the related art, which will not be described here again.

Referring to FIG. 1, in order to facilitate manufacturing of the first ring 11a and the second ring 12a, the penis sleeve part 10 further includes a first connecting part 14 in a specific embodiment. Two ends of the first connecting part 14 are respectively arranged on the first ring 11a and the second ring 12a for flexibly connecting the first ring 11a and the second ring 12a.

In a specific embodiment, the first connecting part 14 is of rubber, and is integrally formed with the first ring 11a and the second ring 12a.

Figure 4:
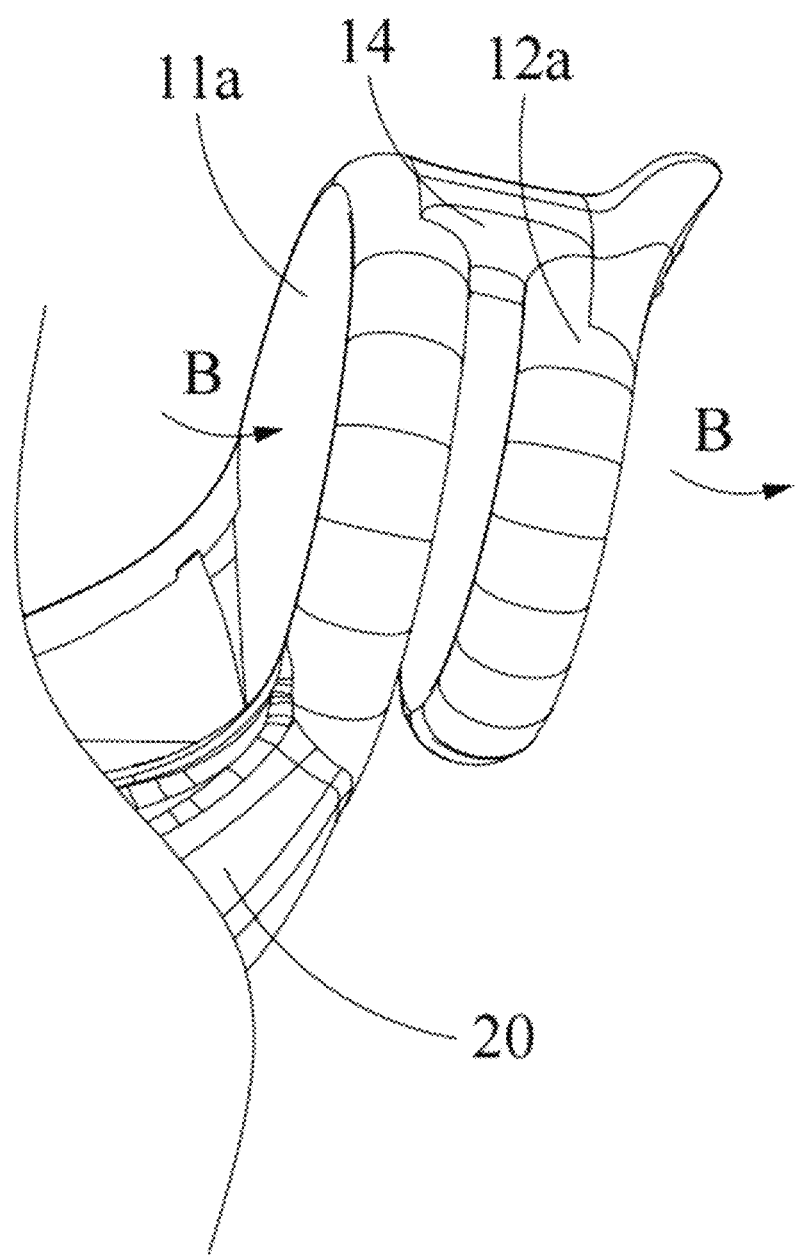
FIG. 4 is a schematic perspective structural view of a cock ring according to another embodiment of the present disclosure.

In another embodiment, specifically referring to FIG. 4, the penis sleeve part 10 is also constructed by the first ring 11a and the second ring 12a. When in use, the penis is inserted into the first ring 11a and the second ring 12a in a direction of B-B as shown in FIG. 4. Preferably, a structure of the embodiment shown in FIG. 4 is more convenient to be inserted than that of the embodiment shown in FIGS. 1 to 3.

Figure 5:
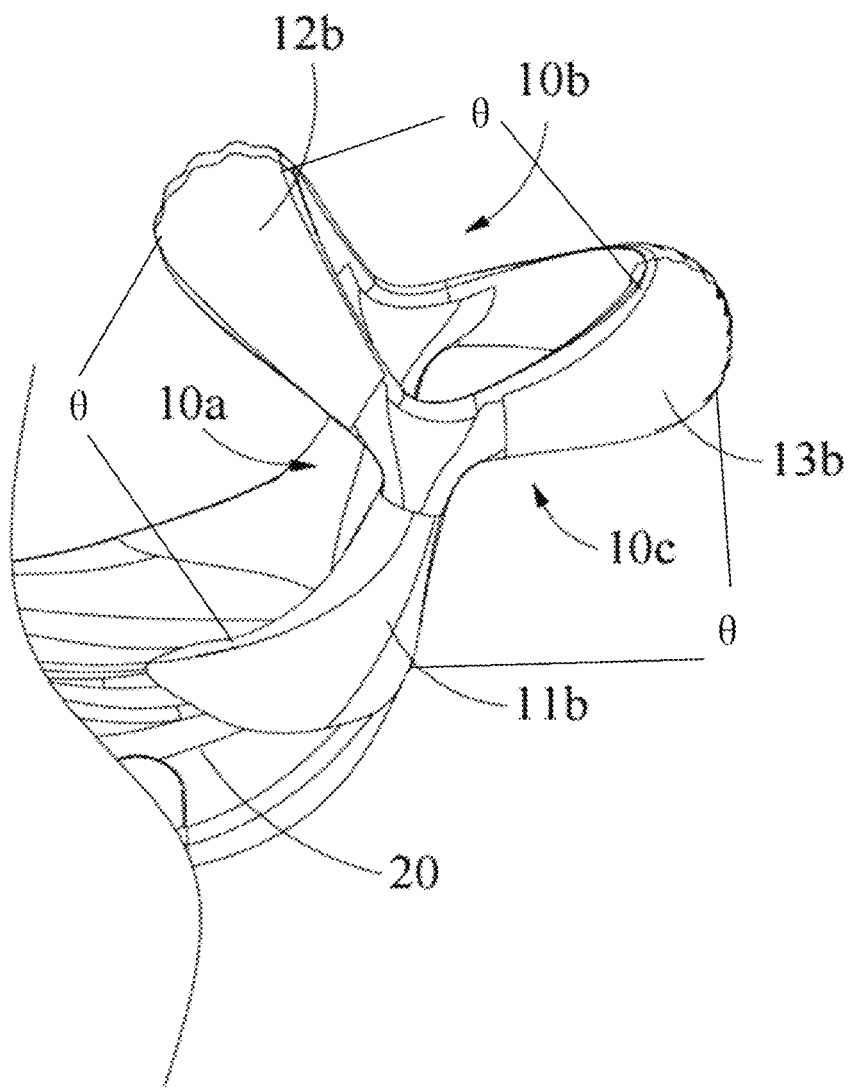
FIG. 5 is a schematic perspective structural view of a cock ring according to a third embodiment of the present disclosure.

In the third embodiment, referring to FIG. 5, the penis sleeve 10 includes a first ring 11b, a second ring 12b and a third ring 13b. Two end of the first ring 11b are respectively arranged on the first stimulating part 20 to enclose to form a first opening 10a, two ends of the second ring 12b are respectively arranged on the first ring 11b, and two ends of the third ring 13b are respectively arranged on the first ring 11b, and the second ring 12b and the third ring 13b enclose to form a second opening 10b, and the third ring 13b and the first ring 11b enclose to form a third opening 10c. The penis is inserted through the first opening 10a and the second opening 10b, and the testis or perineum is carried between the first opening 10a and the third opening 10c and abuts against the first stimulating part 20.

In the third embodiment described above, by providing the first ring 11b, the second ring 12b and the third ring 13b and cooperating the first ring 11b, the second ring 12b and the third ring 13b to encircle and lock the penis, higher encircling tightness can be obtained compared with encircling of two rings, so that better effect of preventing blood backflow can be achieved, and compared with cooperation of two rings, cooperation of three rings can avoid a problem of insecure sleeving of the penis caused by left and right shaking when the penis is sleeved.

In a specific embodiment, the first ring 11b, the second ring 12b and the third ring 13b are annularly arranged at equal intervals.

In a specific embodiment, the first stimulating part 20 includes an accommodating part 21 and an abutting part 22. The accommodating part 21 is provided with a first accommodating cavity for accommodating a stimulation component, and the abutting part 22 is attached to the accommodating part 21 for contacting and abutting against the testis or perineum.

Figure 6:
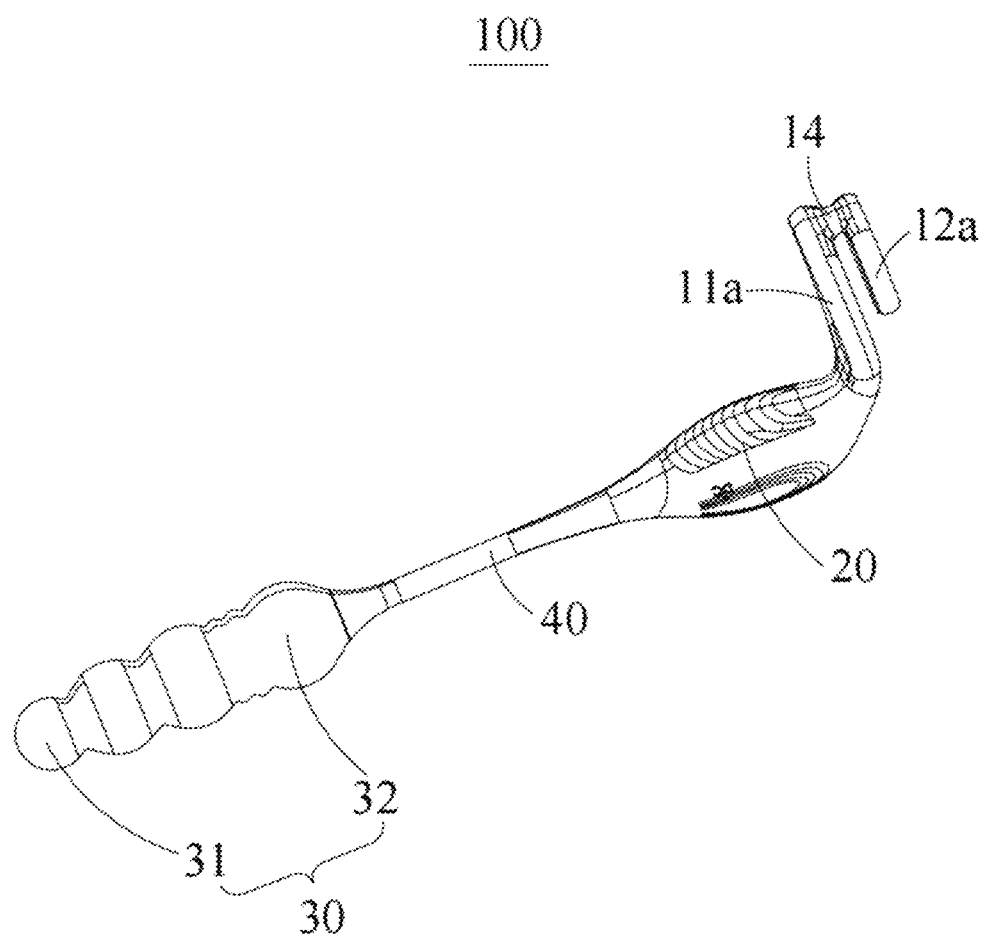
FIG. 6 is a schematic perspective structural view of a cock ring according to a forth embodiment of the present disclosure.

In the fourth embodiment, specifically referring to FIG. 6, a shape of the second stimulating part 30 is different from that in the embodiment above.

Specifically, the accommodating part 21 and the abutting part 22 is in an integrated structure. The accommodating part 21 is configured for accommodating the stimulation component to generate stimulation, and the abutting part 22 is configured for contacting the testis or perineum. When the accommodating part 21 generates stimulation, a stimulation source of the accommodating part 21 is transmitted to the abutting part 22 and to the testis or perineum.

In a specific embodiment, the abutting part 22 includes a plurality of protrusions 221, and the plurality of protrusions 221 are arranged in parallel for contacting and abutting against the testis or perineum. It can be understood that the plurality of protrusions 221 are arranged in parallel to form a grid-like surface, so that when the testicles or perineum contacts and abuts against the abutting part 22, better health care effect can be achieved and placement comfort at the testicles or perineum can be improved due to the grid-like undulating structure.

Further, in order to facilitate inserting of the second stimulating part 30 into the anus, in a specific embodiment, the second stimulating part 30 includes an inserting end 31 and a stimulating end 32. The insertion end 31 is configured to be inserted into anus of a human body, and the stimulation end 32 is provided with a second accommodating cavity for accommodating a stimulation component. A cross-sectional area of the insertion end 31 gradually increases in a direction from the insertion end 31 to the stimulation end 32.

Specifically, in the first to third embodiments, the insertion end 31 and the stimulation end 32 together form a bullet-like structure, that is, with a small front end and a large rear end. Therefore, in a process of inserting the second stimulating part into the anus, the insertion end 31 has a small cross-sectional area, which reduces friction in insertion into the anal, thus facilitating the insertion into the anal. The stimulation end 32 is configured for holding the stimulation component and is with a larger cross-sectional area than that of the insertion end 31, so that when the stimulation end 32 extends into the anus, it has a large stimulation area due to its large volume, thereby improving its stimulation effect.

In the fourth embodiment, the insertion end 31 and the stimulation end 32 are generally in a ball-connected shape.

Further, in order to facilitate insertion of the second stimulating part 30 into the anus when the penis sleeve part 10 is sleeved on the penis, in a specific embodiment, the cock ring 100 further includes a second connecting part 40, and both ends of the second connecting part 40 are respectively arranged on the first stimulating part 20 and the second stimulating part 30.

It can be understood that by providing the second connecting part 40, a certain distance is formed between the penis sleeve part 10 and the second stimulating part 30, so that when the penis sleeve part 10 is sleeved on the penis, the second stimulating part 30 can bypass the crotch of the human body and extends and is inserted into the anus.

In a specific embodiment, the second connecting part 40 is a flexible strip structure for the second stimulating part 30 to be bent relative to the first stimulating part 20. Preferably, the second connecting part 40 is made of rubber or silica gel and is integrally formed with the first stimulating part 20 and the second stimulating part 30.

The above is only implementations of this disclosure, and it should be noted herein that improvements can be made for those of ordinary skilled in the art without departing from the concept of this disclosure, which belong to the protection scope of this disclosure.

What is claimed is:

1. A cock ring, comprising a penis sleeve part, a first stimulating part and a second stimulating part which are flexibly provided in sequence; wherein the penis sleeve part is configured to be sleeved on penis, the first stimulating part is configured to contact and abut against testis or perineum for stimulating the testis or perineum, and the second stimulating part is configured to be inserted into the anus for stimulating the anus;

the second stimulating part comprises an insertion end and a stimulation end, and a cross-sectional area of the insertion end gradually increases in a direction from the insertion end to the stimulation end; and a distance between the first stimulating part and the second stimulating part is adjustable;

wherein the penis sleeve part comprises a first ring, a second ring and a third ring; wherein the first ring, the second ring and the third ring are annularly arranged at equal intervals; wherein two end of the first ring are respectively arranged on the first stimulating part to enclose to form a first opening, two ends of the second ring are respectively arranged on the first ring, and two ends of the third ring are respectively arranged on the first ring, and the second ring and the third ring enclose to form a second opening, and the third ring and the first ring enclose to form a third opening.

2. The cock ring according to claim 1, wherein the first stimulating part comprises an accommodating part and an abutting part; wherein the accommodating part is provided with a first accommodating cavity for accommodating a stimulation component, and the abutting part is attached to the accommodating part for contacting and abutting against the testis or perineum.

3. The cock ring according to claim 2, wherein the abutting part comprises a plurality of protrusions, and the plurality of protrusions are arranged in parallel for contacting and abutting against the testis.

4. The cock ring according to claim 1, wherein the second stimulation part comprises an insertion end and a stimulation end; wherein the insertion end is configured to be inserted into anus of a human body, and the stimulation end is provided with a second accommodating cavity for accommodating a stimulation component; and wherein a cross-sectional area of the insertion end gradually increases in a direction from the insertion end to the stimulation end.

5. The cock ring according to claim 1, wherein the cock ring further comprises a second connecting part, and both ends of the second connecting part are respectively arranged on the first stimulating part and the second stimulating part.

6. The cock ring according to claim 5, wherein the second connecting part is a flexible strip structure for the second stimulating part to be bent relative to the first stimulating part.

* * * * *